(12) United States Patent
Jonaitis et al.

(10) Patent No.: US 7,323,451 B2
(45) Date of Patent: Jan. 29, 2008

(54) CRYSTALLINE AND AMORPHOUS FORMS OF BETA-L-2'-DEOXYTHYMIDINE

(75) Inventors: David Jonaitis, West Lafayette, IN (US); Richard Storer, Folkestone (GB)

(73) Assignee: Idenix Pharmaceuticals, Inc., Cambridge, MA (US)

( * ) Notice: Subject to any disclaimer, the term of this patent is extended or adjusted under 35 U.S.C. 154(b) by 17 days.

(21) Appl. No.: 10/636,349

(22) Filed: Aug. 6, 2003

(65) Prior Publication Data

US 2004/0087541 A1 May 6, 2004

Related U.S. Application Data

(60) Provisional application No. 60/401,318, filed on Aug. 6, 2002.

(51) Int. Cl.
| | |
|---|---|
| A01N 43/04 | (2006.01) |
| A61K 31/70 | (2006.01) |
| C07H 21/00 | (2006.01) |
| C07H 21/02 | (2006.01) |
| C07H 21/04 | (2006.01) |

(52) U.S. Cl. .......................... 514/45; 514/43; 514/46; 514/47; 536/27.8

(58) Field of Classification Search ................ 514/45, 514/46, 47, 43; 536/27.8
See application file for complete search history.

(56) References Cited

U.S. PATENT DOCUMENTS

| | | | |
|---|---|---|---|
| 4,916,122 A | 4/1990 | Chu | |
| 4,957,924 A | 9/1990 | Beauchamp | |
| 5,149,794 A | 9/1992 | Yatvin et al. | |
| 5,190,926 A | 3/1993 | Chu | |
| 5,194,654 A | 3/1993 | Hostetler et al. | |
| 5,220,003 A | 6/1993 | Jung et al. | |
| 5,223,263 A | 6/1993 | Hostetler et al. | |
| 5,256,641 A | 10/1993 | Yatvin et al. | |
| 5,411,947 A | 5/1995 | Hostetler et al. | |
| 5,463,092 A | 10/1995 | Hostetler et al. | |
| 5,539,116 A | 7/1996 | Liotta | |
| 5,543,389 A | 8/1996 | Yatvin et al. | |
| 5,543,390 A | 8/1996 | Yatvin et al. | |
| 5,543,391 A | 8/1996 | Yatvin et al. | |
| 5,554,728 A | 9/1996 | Basava et al. | |
| 5,559,101 A | 9/1996 | Weis et al. | |
| 5,565,438 A | 10/1996 | Chu | |
| 5,567,688 A | 10/1996 | Chu | |
| 5,587,362 A | 12/1996 | Chu | |
| 5,939,402 A | 8/1999 | Weis et al. | |
| 5,990,093 A | 11/1999 | Schinazi et al. | |
| 6,025,335 A | 2/2000 | Weis et al. | |
| 6,194,391 B1 | 2/2001 | Schinazi et al. | |
| 6,245,749 B1 | 6/2001 | Schinazi et al. | |
| 6,297,222 B1 | 10/2001 | von Borstel et al. | |
| 6,395,716 B1 * | 5/2002 | Gosselin et al. ............... 514/45 |
| 6,444,652 B1 | 9/2002 | Gosselin et al. | |
| 6,462,174 B1 * | 10/2002 | Roberts ....................... 530/331 |
| 6,566,344 B1 | 5/2003 | Gosselin et al. | |
| 6,569,837 B1 | 5/2003 | Gosselin et al. | |
| 6,723,728 B2 * | 4/2004 | Hu et al. ..................... 514/274 |

FOREIGN PATENT DOCUMENTS

| | | |
|---|---|---|
| CA | 2 206 878 A1 | 3/1997 |
| EP | 0 350 287 A2 | 1/1990 |
| EP | 0 352 248 A1 | 1/1990 |
| EP | 0 494 119 A1 | 7/1992 |
| EP | 0 355 131 B1 | 9/1996 |
| GB | 875 971 | 8/1961 |
| JP | 6-293645 A | 10/1994 |
| WO | WO89/02733 A1 | 4/1989 |
| WO | WO89/03838 A1 | 5/1989 |
| WO | WO90/00555 A1 | 1/1990 |
| WO | WO91/16920 A1 | 11/1991 |
| WO | WO91/18914 A1 | 12/1991 |
| WO | WO91/19721 A1 | 12/1991 |
| WO | WO92/08727 A1 | 5/1992 |
| WO | WO92/15308 A1 | 9/1992 |
| WO | WO92/18517 A1 | 10/1992 |
| WO | WO93/00910 A1 | 1/1993 |
| WO | WO 94/01138 A1 | 1/1994 |
| WO | WO94/20523 A1 | 9/1994 |
| WO | WO94/26273 A1 | 11/1994 |
| WO | WO95/07086 A1 | 3/1995 |
| WO | WO96/11204 A1 | 4/1996 |
| WO | WO96/13512 A2 | 5/1996 |

(Continued)

OTHER PUBLICATIONS

Legeay et al. Eur. Polym. J. (1998), vol. 34, No. 10, pp. 1457-1465.*
Arner, E.S.J., et al., "Mammalian Deoxyribonicleoside Kinases," *Pharm. Ther.*, 67(2), 155-186 (1995).
Berk, A.J., et al., "A Genetically Distinct Tymidine Kinase in Mammalian Mitochondria," *J Biol Chem*, 248(8):2722-2729 (1973).
Bestwick, R.K., et al., "Selective Expansion of Mitochondrial Nucleoside Triphosphate Pools in Antimetabolite-treated HeLa Cells," *J. Biol. Chem.*, 257(16):9300-9304 (1982).
Bloch, A., et al. "The Role Of The 5'-Hydroxyl Group Of Adenosine In Determining Substrate Specificity For Adenosine Deaminase," *J. Med. Chem.*, 10(5):908-12 (Sep. 1967).
Bridges, E.G., et al., "Characterization of a dCTP Transport Activity Reconstituted from Human Mitochondria," *J. Biol. Chem.*, 274(8):4620-4625 (Feb. 19, 1999).

(Continued)

*Primary Examiner*—Patrick Lewis
(74) *Attorney, Agent, or Firm*—Jones Day (57) ABSTRACT

Physical forms of beta-L-2'-deoxythymidine are disclosed that can be characterized by physical appearance, purity levels, Infra-Red and Raman spectroscopy, X-ray powder diffraction patterns, thermal properties, and methods of manufacture. These forms of beta-L-2'-deoxythymidine can be used in the manufacture of other forms of beta-L-2'-deoxythymidine, or in pharmaceutical compositions. Particularly preferred uses are in the treatment of hepatitis B.

15 Claims, 8 Drawing Sheets

FOREIGN PATENT DOCUMENTS

| | | |
|---|---|---|
| WO | WO96/15132 A1 | 5/1996 |
| WO | WO96/40164 A1 | 12/1996 |
| WO | WO 99/45935 A1 | 9/1999 |
| WO | WO 00/09531 A2 | 2/2000 |

OTHER PUBLICATIONS

Bridges, E.G., et al., "Identification of a novel mitochondrial dNTP carrier and its interaction with anti-HIV nucleoside analogs," *Proc. Am. Assoc. Cancer Res.*, 38:414 (Mar. 1997).

Bridges, E.G., et al., "Inhibition of Mammalian DNA Polymerase-Associated 3' to 5' Exonuclease Activity by 5'-Monophosphates of 3'-Azido-3'-Deoxythymine and 3'-Amino-3'-Deoxythymidine," *Biochemical Pharmacology*, 45(8):1571-1576 (1993).

Bryant, M.L., et al., "Antiviral L-Nucleosides Specific for Hepatitis B Virus Infection," *Antimicrobial Agents and Chemotherapy*, 45(1):229-235 (Jan. 2001).

Chang, C.N., et al., "Deoxycytidine Deaminase-resistant Stereoisomer is the Active Form of (−)-2',3'-thiacytidine in the Inhibition of Hepatitis B Virus Replication," *Journal of Biological Chemistry*, 267(20):13938-13942 (Jul. 15, 1992).

Chang, C.-N., et al., "Biochemical Pharmacology of (+)- and (−)-2',3'-Dideoxy-3'-thiacytidine as Anti-hepatitis B Virus Agents," *J Biol Chem*, 267(31), 22414-22420 (Nov. 5, 1992).

Chariot, P., et al., "Zidovudine-induced mitochondrial disorder with massive liver steatosis myopathy, lactic acidosis, and mitochondrial DNA depletion," *J. Hepatology*, 30:156-160 (1999).

Chen, M.S., et al., "Characterization of Pyrimidine Deoxyribonucleoside Kinase (Thymidine Kinase) and Thymidylate Kinase as a Multifunctional Enzyme in Cells Transformed by Herpes Simplex Virus Type 1 and in Cells Infected with Mutant Strains of Herpes Simplex Virus," *J Virol.*, 30(3):942-945 (Jun. 1979).

Chen, C.-H., et al., "Delayed Cytotoxicity and Selective Loss of Mitochondrial DNA in Cells Treated with the Anti-human Immunodeficiency Virus Compound 2',3'-Dideoxycytidine," *J. Biol. Chem.*, 264(20):11934-11937 (Jul. 15, 1989).

Chen, C.-H., et al., "The Role of Cytoplasmic Deoxycytidine Kinase in the Mitochondrial Effects of the Anti-human Immunodeficiency Virus Compound 2',3'-Dideoxycytine," *J. Biol. Chem.*, 267(5): 2856-2859 (Feb. 15, 1992).

Cui, L., et al., "Effect of Nucleoside Analogs on Neurite Regeneration and Mitochondrial DNA Synthesis in PC-12 Cells," *J. of Pharmacology and Experimental Therapeutics*, 280(3):1228-1234 (1997).

Davis, A.F., et al., "In Situ Localization of Mitochondrial DNA Replication in Intact Mammalian Cells," *J Cell Biol*, 135(4), 883-893 (Nov. 1996).

Doong, S.-L., et al., "Inhibition of the replication of hepatitis B virus *in vitro* by 2',3'-dideoxy-3'-thiacytidine and related analogues," *Proc. Natl. Acad. Sci. USA*, 88:8495-8499 (Oct. 1991).

Du, J., et al, Synthesis, "Anti-Human Immunodeficiency Virus and Anti-Hepatitis B Virus Activities of Novel Oxaselenolane Nucleosides," *J. of Med. Chem.*, (40)19:2991-2993 (Sep. 12, 1997).

Dutschman, G.E., et al., "Metabolism of 2',3'-dideoxy-2',3'-didehydro-β-L-(−)-5-Fluorocytidine and Its Activity in Combination with Clinically Approved Anti-Humna Immunodeficiency Virus β-D-(+) Nucleoside Analogs In Vitro," *Antimicrobial Agents and Chemotherapy*, 42(7), 1799-1804 (Jul. 1998).

Furman, P.A., et al., "The Anti-Hepatitis B Virus Activities, Cytotoxicities, and Anabolic Profiles of the (−) and (+) Enantiomers of *cis*-5-Fluoro-1-[2-(Hydroxymethyl)-1,3-oxathiolane-5-yl]-Cytosine" *Antimicrobial Agents and Chemotherapy*, 36(12):2686-2692 (Dec. 1992).

Hernandez-Santiago, B., et al., "Pharmacology of β-L-Thymidine and β-L-2'-Deoxycytidine in HepG2 Cell and Primary Human Hepatocytes: Relevance to Chemotherapeutic Efficacy against Hepatitis B Virus," *Antimicrobial Agents and Chemotherapy*, 46(6), 1728-1733 (Jun. 2002).

Hoard, D.E., et al., "Conversion of Mono- and Oligodeoxyribonucleotides to 5'-Triphosphates," *J. Am. Chem. Soc.*, 87(8):1785-1788 (Apr. 20, 1965).

Holy, A., "Nucleic Acid Components and Their Analogs. CLIII. Preparation of 2'-deoxy-L-Ribonucleosides of the Pyrimidine Series," *Collect. Czech. Chem. Commun.*, 37(12):4072-4087 (1972).

Hostetler, K.Y., et al. "Synthesis And Antiretroviral Activity Of Phospholipid Analogs Of Azidothymidine And Other Antiviral Nucleosides," *J. Biol Chem.*, 265(11):6112-6115 (Apr. 15, 1990).

Hostetler, K.Y., et al. "Greatly Enhanced Inhibition Of Human Immunodeficiency Virus Type 1 Replication In CEM And HT4-6C Cells By 3'-Deoxythymidine Diphosphate Dimyristoylglycerol, A Lipid Prodrug Of 3'-Deoxythymidine," *Antimicrob Agents Chemother.*, 36(9):2025-2029 (Sep. 1992).

Jones, R.J., et al., "Mini Review: Nucleotide prodrugs," *Antiviral Research*, 27:1-17 (1995).

Jurovcik, W., et al., "Metabolism of pyrimdine L-nucleosides," *Nucleic Acids Research*, 3(8), 2143-2154 (Aug. 1976).

Korba, B.E., et al., "A cell culture assay for compounds which inhibit hepatitis B virus replication," *Antiviral Res.*, 15:217-228 (1991).

Krayevsky, A.A., et al., "Can a Substrate Enantiomer Be a Substrate for the Same Enzyme?," *Molecular Biology*, 30(5, Part 1):585-591 (1996).

Krayevsky A.A., et al., "Should the Asymmetry of Enzymatic Active Centers Always Correlate with the Asymmetry of their Substrates?," *J. of Bionolecular Structure & Dynamics*, 14(2):225-230 (1996).

Labenz, J., et al., "Analysis of the TK Enzyme Complex Induced by HSV Types 1 and 2 by Means of Isoelectric Focusing and Polyacyrlamide Gel Electrophoresis," *Arch. Virol.*, 71:235-249 (1982).

Lin, T.-S., et al., "Synthesis and Biological Evaluation of 2',3'-Dideoxy-L-pyrimidine Nucleosides as Potential Antiviral Agents agains HIV and HBV," *J. Med. Chem.*, 37:798-803 (1994).

Lin, T.-S., et al., "Synthesis of Several Pyrimidine L-Nucleoside Analogues as Potential Antiviral Agents," *Tetrahedron Letters*, 51(4):1055-1068 (1995).

Lin, T.S., et al., "Design and Synthesis of 2',3'-Dideoxy-2',3'-didehydro-β-L-cytidine (β-L-d4C) and 2',3'-Dideoxy-2',3'-didehydro-β-L-5-fluorocytidine (β-L-Fd4C), Two Exceptionally Potent Inhibitors of Human Hepatitis B Virus (HBV) and Potent Inhibitors of Human Immunodeficiency Virus (HIV) In Vitro," *J. Med. Chem.*, 39(9):1757-1759 (Apr. 26, 1996).

Maga, G., et al., "Lack of stereospecificity of suid pseudorabies virus thymidine kinase," *Biochem. J.*, 294(2):381-385 (Sep. 1, 1993).

Norbeck, D.W., et al., "A new 2',3'-dideoxynucleoside prototype with in vitro activity against HIV," *Tetrahedron Letters*, 30(46):6263-6266 (1989).

Pan-Zhou, X.-R., et al., "Differential Effects of Antiretroviral Nucleoside Analogs on Mitochondrial Function in HepG2 Cells," *Antimicrobial Agents and Chemotherapy*, 44(3):496-503 (Mar. 2000).

Placidi, et al., "Cellular pharmacology of β-L-thymidine and β-L-2'-deoxycytidine in HepG2 cells and primary rat, monkey and human hepatocytes," *Antivir. Ther.*, 4(Suppl.4):46-47, abstract A122 (3$^{rd}$ *Int. Conf. Ther. Vir. Hepatitis*) (1999).

Robins, M. J., et al., "Purine nucleosides. XXIX. The synthesis of 2'-deoxy-L-adenosine and 2'-deoxy-L-guanosine and their α anomers," *J. Org. Chem.*, 35(3):636-639 (Mar. 1970).

Robins, M.J., et al., "Selective Deoxygenation and Modification at C2' of Nucleosides," *Nucleic Acids Research Symposium Series*, vol. 11, pp. 1-4, Kyoto, Japan, Nov. 24-26, 1982, A.E. Pritchard (ed.), IRL Press, Ltd., Oxford, England, 1982 [Chemical Abstracts Service, No. 98:10767u].

Robins, M.J., et al., "Nucleic Acid Related Compounds. 42. A General Procedure for the Efficient Deoxygenation of Secondary Alcohols. Regiospecific and Stereoselective Conversion of Ribonucleosides to 2'-Deoxynucleosides," *J. Am. Chem. Soc.*, 105:4059-4065 (1983).

Schinazi, R.F., et al., "Effect of Combinations of Acylovir with Vidarabine or its 5'-Monophosphate on Herpes Simplex Viruses in Cell Culture and in Mice," *Antimicrobial Agents and Chemotherapy*, 22(3):499-507 (Sep. 1982).

Schinazi, R.F., et al., "Selective Inhibition of Human Immunodeficiency Viruses by Racemates and Enantiomers of *cis*-5-Fluoro-1-[2-(Hydroxymethyl)-1,3-Oxathiolane-5-yl] Cytosine," *Antimicrobial Agents and Chemotherapy*, 36(11):2423-2431 (Nov. 1992).

Shuto, S., et al., "A facile one-step synthesis of 5'-phosphatidylnucleosides by an enzymatic two-phase reaction," *Tetrahedron Letters*, 28(2):199-202 (1987).

Söderlund, J.C.F., "Mitochondrial versus cytosolic activities of deoxyribonucleoside salvage enzymes," in *Purine and Pyrimidine Metabolism in Man VIII*, A.Shota & M. Taylor (Eds.), Plenum Press, New York, 1995, pp. 201-204.

Spadari, S., et al., "L-Thymidine is Phosphorylated by Herpes Simplex Type 1 Thymidine Kinase and Inhibits Viral Growth," *J. Med. Chem.*, 35(22):4214-4220 (1992).

Verri, A., et al., "Lack of enantiospecificity of human 2'-deoxycytidine kinase: relevance for the activation of β-L-deoxycytidine analogs as antineoplastic and antiviral agents," *Molecular Pharmacology*, 51(1):132-138 (Jan. 1997).

Verri, A., et al., "Relaxed Enantioselectivity of Human Mitochondrial Thymidine Kinase and Chemotherapeutic Uses of L-Nucleoside Analogues," *Biochem. J.*, 328(1):317-320 (Nov. 15, 1997).

Von Janta-Lipinski, M., et al., "Newly Synthesized L-Enantiomers of 3'-Fluoro-Modified β-2'-Deoxyribonucleoside 5'-Triphosphates Inhibit Hepatitis B DNA Polymerase but not the Five Cellular DNA Polymerases α, β, γ, δ, and ε Nor HIV-1 Reverse Transcriptase," *J. Medicinal Chemistry*, 41(12):2040-2046 (May 21, 1998).

Zedeck, M.S., et al., "Inhibition of the steroid-induced synthesis of D5-3-ketosteroid isomerase in *Pseudomonas testosterone* by a new purine deoxyribonucleoside analog: 6-chloro-8-aza-9-cyclopentylpurine," *Mol. Pharmacol.*, 3(4):386-395 (1967).

Zhu, Y.-L., et al., "Inhibition of Replication of Hepatitis B Virus by Cytallene In Vitro," *Antimicrobial Agents and Chemotherapy*, 41(8):1755-1760 (Aug. 1997).

Zhu, Y.-L., et al., "Anti-Hepatitis B Virus Activity and Metabolism of 2',3'-dideoxy-2',3'-didehydro-β-L-(−)-5-Fluorocytidine," *Antimicrobial Agents and Chemotherapy*, 42(7):1805-1810 (Jul. 1998).

Zhu, C., et al., "Incorporation of Nucleoside Analogs into Nuclear or Mitochondrial DNA Is Determined by the Intracellular Phosphorylation Site," *J Biol Chem*, 275(35):26727-26731 (2000).

Davisson et al Synthesis of Nucleotide 5'-Diphosphates from 5'-0-Tosyl Nucleosides, *Journal of Organic Chemistry*, vol. 52 (9), pp. 1794-1801 Jan. 1, 1987.

Farci et al Treatment of Chronic Hepatitis D with Interferon Alfa-2a, *The New England Journal of Medicine*, vol. 330 (1), pp. 88-94 Jan. 13, 1994.

Fujimori et al Enantio-Oligodeoxyribonucleosides, Symposium on Nucleic Acids Technology, *Nucleic Acids Research Symposium Series*, vol. 22, pp. 97-98 Jan. 1, 1990.

Gosselin et al Synthesis and Antiviral Evaluation of β-L-Xylofuranosyl Nucleosides of the Five Naturally Occuring Nucleic Acid Bases, *Journal of Heterocyclic Chemistry*, vol. 30, pp. 1229-1233 Oct. 1, 1993.

Imai et al Studies on Phosphorylation. IV. Selective Phosphorylation of the Primary Hydroxyl Group in Nucleosides, *Journal of Organic Chemistry*, vol. 34 (6), pp. 1547-1550 Jun. 1, 1969.

Kucera et al Novel Membrane-Interactive Ether Lipid Analogs that Inhibit Infectious HIV-1 Production and Induce Defective Virus Formation, *AIDS Research and Human Retroviruses*, vol. 6 (4), pp. 491-501 May 1, 1990.

Mansour et al Stereochemical Aspects of the Anti-HCMV Activity of Cytidine Nucleoside Analogues, *Antiviral Chemistry & Chemotherapy*, vol. 6 (3), pp. 138-142 Jan. 1, 1995.

Nakayama et al Synthetic Nucleosides and Nucleotides. XX. Synthesis of Various 1-β-D-Xylofuranosyl-5-Alkyluracils and Related Nucleosides, *Nucleosides and Nucleotides*, vol. 1 (2), pp. 139-146 Jan. 1, 1982.

Saneyoshi et al Synthetic Nucleosides and Nucleotides. XIII. Stannic Chloride Catalyzed Ribosylation of Several 6-Substituted Purines, *Chemical and Pharmaceutical Bulletin*, vol. 27, pp. 2518-2521 Jan. 1, 1979.

Tyrsted et al Inhibition of the Synthesis of 5-Phosphoribosyl-1-Pyrophosphate by 3'- Deoxy- adenosine and Structurally Related Nucleoside Analogs, *Biochimica et Biophysica Acta*, vol. 155 (2), pp. 619-622 Feb. 26, 1968.

Voet et al. Absorption Spectra of Nucleotides, Polynucleotides, and Nucleic Acids in the Far Ultraviolet, *Bioploymers*, vol. 1, pp. 193-208 Jan. 1, 1963.

Wang et al. Recovery of Liver Sinusoidal Endothelial Cell Function over Time after Hypothermic Preservation in Rat Orthotopic Liver Transplantation, *Hepatology (AASLD Abstracts -Abstract No: 1219)*, vol. 24 (4, Pt 2), p. 431A Jan. 1, 1996.

Zhang et al Removal of Silyl Protecting Groups from Hydroxyl Functions with Ammonium Fluoride in Methanol, *Tetrahedron Letters*, vol. 33 (9), pp. 1177-1180 Jan. 1, 1992.

\* cited by examiner

Figure 1. XRPD patterns of crystalline L-dT and amorphous L-dT

Figure 2. IR spectra for crystalline and amorphous L-dT

Figure 3. Raman spectra for crystalline and amorphous L-dT

FIG. 4

Figure 5. Moisture sorption data for crystalline L-dT

Figure 8. Moisture sorption/desorption curves for amorphous L-dT

CRYSTALLINE AND AMORPHOUS FORMS OF BETA-L-2'-DEOXYTHYMIDINE

CROSS-REFERENCE OF THE INVENTION

This application claims priority to U.S. Provisional Application Ser. No. 60/401,318, filed on Aug. 6, 2002.

FIELD OF THE INVENTION

The present invention describes crystalline and amorphous forms of beta-L-2'-deoxythymidine and mixtures thereof, substantially pure crystalline and amorphous forms of beta-L-2'-deoxythymidine, analytical methods for confirming the presence and crystalline purity of beta-L-2'-deoxythymidine, pharmaceutical compositions thereof, and uses for such compositions.

BACKGROUND OF THE INVENTION

The synthetic nucleoside beta-L-2'-deoxythymidine (L-dT) is known in the art. Antonin Holy first disclosed beta-L-2'-deoxythymidine and methods for preparing beta-L-2'-deoxythymidine in 1972 in "Nucleic Acid Components and Their Analogs. CLIII. Preparation of 2'-deoxy-L-Ribonucleosides of the Pyrimidine Series," *Collect. Czech. Chem. Commun.* (1972), 37(12), 4072–87. The compound is represented by the following chemical structure:

wherein R is H.

Several authors have reported antiviral activity of beta-L-2'-deoxythymidine against herpes simplex virus. See, e.g., Iotti et al., WO 92/08727; and Spadari et al., *J. Med. Chem.* (1992), 35(22), 4214–20.

More recently, Gilles Gosselin, Jean-Louis Imbach and Martin Bryant disclosed that the compound and its derivatives and analogues have useful properties against the hepatitis B virus. See WO 00/09531; PCT US01/17301 and PCT US01/19147; U.S. Pat. Nos. 6,395,716; 6,569,837; 6,444,652; and 6,566,344. L-dT is currently in advanced clinical development by Idenix Pharmaceuticals, Inc. (Cambridge, Mass.).

Each of the foregoing references discloses a synthetic process for producing L-dT that relies upon crystallizing the compound from ethanol. None of the references disclose the particular crystalline or physical form of the L-dT that was obtained, or the water content of such L-dT. However, it has been recognized that crystalline, amorphous, hydrated, and various physical forms of the same compound can vary substantially in their biological properties, and in their ease of processing, manufacturing and/or pharmaceutical formulation. In addition, some forms are unstable under ambient conditions and thus require special storage and handling conditions to be maintained, or must be avoided altogether.

Given the commercial importance of beta-L-2'-deoxythymidine, it would be useful to have additional forms and phases of beta-L-2'-deoxythymidine that may exhibit beneficial properties in manufacturing or other applications. It is therefore an objective of this invention to provide novel forms and phases of beta-L-2'-deoxythymidine.

It is another objective to provide novel methods for the preparation and isolation of forms and phases of beta-L-2'-deoxythymidine.

It is still another objective of the invention to provide therapeutic uses of such forms and phases of beta-L-2'-deoxythymidine.

SUMMARY OF THE INVENTION

As a result of studies into the crystalline structure and various physical forms of L-dT, Applicants have unexpectedly made a number of significant discoveries. In particular, Applicants have discovered:

structural forms of crystalline L-dT that can be characterized by their physical appearance;
an amorphous form of L-dT; and
mixtures of these two forms.

These discoveries lead to the production of a form of L-dT that is substantially devoid of water and can be maintained for a period of time, or shelf life, of at least 1, 2, 3, 4, 5, 6, 7, 8, 9, 10 11 or 12 months or more, by maintaining the compound under appropriate conditions of low humidity. Given that nucleosides in general are polar, water soluble compounds, and that L-dT in particular contains a pyrimidinedione ring and two free hydroxy groups, it could not be predicted that L-dT, when substantially devoid of waters of hydration, could be maintained for an extended shelf-life.

In addition, Applicants have discovered methods of analyzing the purity of crystalline L-dT for contamination by amorphous L-dT. These analytical methods include diffractional, vibrational, thermal, and other analytical techniques. In still other embodiments the invention includes methods of making the foregoing forms of L-dT.

These forms of L-dT have advantageous properties in the preparation of pharmaceutical compositions and in the treatment of hepatitis B. Beneficial properties can be attributed to these different physical forms including increased solubility, improved bioavailability, ease of chemical processing and/or ease of pharmaceutical formulation.

DETAILED DESCRIPTION OF THE INVENTION

Anhydrous L-dT Unassociated with Water

A principal embodiment of the present invention derives from the discovery of crystalline beta-L-2'-deoxythymidine, and to methods of preventing the formation of hydrous forms that could affect the stability of the product. The inventors have surprisingly discovered that L-dT, crystallized from ethanol, and then maintained in an environment of less than or equal to about 45% relative humidity, and is substantially impervious to water. The resulting crystalline L-dT is non-solvated and free of adsorbed or absorbed water. As shown from the TG and DK curves in FIG. 4, when L-dT is crystallized and dried in an environment lacking humidity, it is devoid of waters of hydration and association (hence the lack of an endotherm until the substance melts at about 189° C.). As FIG. 5 shows, however, crystalline L-dT will associate with water (via adsorption, absorption or hydration) as the relative humidity exceeds about 45% to 55% relative humidity.

The fact that L-dT devoid of waters of hydration or association can even be obtained is surprising in view of the fact that L-dT is frequently crystallized from ethanol, which necessarily contains water as an impurity at levels greater than about 1, 2, or 3 vol. %, frequently up to about 5, 7, or 10 volume percent. These discoveries led to the invention of L-dT which is substantially devoid of water for a period of time, or shelf life, of at least 1, 2, 3, 4, 5, 6, 7, 8, 9, 10 11 or 12 months or more, by maintaining the compound under appropriate conditions of humidity. Because nucleosides in general are polar, water soluble compounds, and L-dT in particular contains a pyrimidinedione ring and two free hydroxy groups, two carbonyls, a secondary amine, a tertiary amine, and an internal ether linkage, it could not be predicted that L-dT that is devoid of waters of hydration or association could be maintained for an extended shelf-life.

Therefore, in one embodiment the invention provides crystalline L-dT that is substantially devoid of waters of hydration or association, for periods of time exceeding 4, 6, 8, 10, or even 12 months. In another embodiment the invention provides a method of using crystalline L-dT is substantially devoid of water at the end of the time period. The L-dT is preferably administered to a human after such time period. Humid environments include environments in which the relative humidity exceeds greater than about 10%, 20%, 30%, 40%, or 50%, but preferably not more than about 75%, 65%, or 55% relative humidity. The periods of time during which the L-dT can be exposed to such humid environments are greater than 1, 2, 3, 4, 5, 6, 7, 8, 9, 10, 11, or even 12 months, but preferably not more than 3 years, 2 years, or 1½ years. The term "humid environment" means the general ambient conditions to which L-dT or a container of L-dT is exposed. Relative humidities are taken as an average over the recited period of time.

This non-solvated crystalline form of beta-L-2'-deoxythymidine is prepared by crystallizing beta-L-2'-deoxythymidine from solution, optionally filtering said crystallized beta-L-2'-deoxythymidine, and drying said beta-L-2'-deoxythymidine in an environment that lacks humidity (i.e. less than 45%, 40%, 35%, 30%, 25%, 20%, 15%, or 10% relative humidity). The substance is preferably present in the substantial absence of amorphous L-dT.

The term hydrous, when used herein to describe a material, means that the weight of the material is increased by association with water, regardless of the mechanism of association. Thus, the term includes hydrated forms of the material, in addition to material in which water is absorbed or adsorbed. Potential hydrated forms include the monohydrate, the dihydrate, the trihydrate, and the quaternary hydrate.

As used herein, the term, "substantially pure," when used in reference to a physical form, phase or crystalline form of beta-L-2'-deoxythymidine, refers to a phase or form of beta-L-2'-deoxythymidine which is greater than about 95% pure. This means that the phase or form of beta-L-2'-deoxythymidine does not contain more than about 5% of any other compound and, in one embodiment, does not contain more than about 5% of any other phase[s] or form[s] of beta-L-2'-deoxythymidine. In another embodiments, the term "substantially pure" includes a phase or form of beta-L-2'-deoxythymidine that is greater than about 96% pure. In still another embodiment the term "substantially pure" includes a phase or form of beta-L-2'-deoxythymidine that is greater than about 97%, 99%, 99.5%, or 99.8% pure.

Similarly, the term "substantially in the absence of a second component" or "substantially free of a second component" when used in reference to a physical form, phase or crystalline form of beta-L-2'-deoxythymidine, refers to a phase or crystalline form of beta-L-2'-deoxythymidine that does not contain more than about 5% of the second component. More preferably, the term "substantially in the absence of a second component" refers to a phase or form of beta-L-2'-deoxythymidine that does not contain more than about 4% of the second component, and even more preferably no more than about 3%, 1%, 0.5%, or 0.2% of the second component.

Physical Forms of Crystalline L-dT Characterized by their Physical Appearance

In another principal embodiment the invention provides crystalline beta-L-2'-deoxythymidine in various physical forms. Preferred physical forms can be obtained using the methods more fully described in the Examples hereto and include:

white flakes;

clear aciculars;

white aciculars;

white solid;

white powder;

needles;

white chunks;

white fibers; and white plates.

As used herein, the term "flake" is defined as a small flocculent mass of crystals typically in the form of a thin flattened piece or layer. The term "acicular" means a material which incorporates within itself fine, needlelike crystals. A "powder" is a substance composed of fine particles. "Needles" refer to slender pointed objects. A "chunk" refers to a short thick piece often crudely or roughly formed. A "fiber" refers to a structure or object resembling a thread. "Plates" refer to smooth, substantially flat and relatively thin pieces of material. A "solid" material refers to a uniform continuous mass of material obtained upon vaporization of solvent.

The differing physical properties of these physical forms can give rise to numerous unexpectedly beneficial properties including increased solubility, improved bioavailability, ease of chemical processing, and/or ease of pharmaceutical formulation.

In a preferred embodiment, one or more of the foregoing forms is present in its preferred orientation. Preferred orientation is the tendency for crystals, usually plates or needles, to align themselves with some degree of order. In various embodiments, the foregoing physical forms are further characterized by purity levels. For example, in one embodiment the crystalline beta-L-2'-deoxythymidine is substantially free of amorphous beta-L-2'-deoxythymidine.

Still other embodiments relate to methods of manufacturing the foregoing physical forms of beta-L-2'-deoxythymidine. These methods generally require dissolution of beta-L-2'-deoxythymidine in an appropriate solvent, followed by crystallization using one of various techniques. A particularly preferred solvent is ethanol, and especially absolute ethanol, although other solvents can be employed including acetone, acetonitrile, dichloromethane, N,N-dimethylformamide, ethyl acetate, ethyl ether, 1,1,1,3,3,3-hexafluoroisopropanol, hexane, isoproponal, methanol, tetrahydrofuran, toluene, 2,2,2-trifluoroethanol, and water, or mixtures of the foregoing solvents with water.

While numerous methods for crystallizing a solute are known and can be employed in the practice of this invention, particularly preferred methods of recrystallization include:
  crystallizing said dissolved beta-L-2'-deoxythymidine via fast evaporation (i.e. evaporation in an open container under ambient conditions);
  crystallizing said dissolved beta-L-2'-deoxythymidine via slow evaporation (i.e. evaporation in a substantially closed container containing only small holes for escape of vapors under ambient conditions);
  crystallizing said dissolved beta-L-2'-deoxythymidine via slow cooling from an elevated temperature (preferably of about 45–60° C.) under substantially ambient conditions (the dissolution is preferably performed at an elevated temperature, followed by rapid filtration of the dissolved beta-L-2'-deoxythymidine before the slow cooling);
  crystallizing said dissolved beta-L-2'-deoxythymidine via crash cooling;
  crystallizing said dissolved beta-L-2'-deoxythymidine via slurry methods.

Ambient conditions in any of the methods of crystallization can be altered in terms of temperature (i.e. greater than 10° C., 20° C., or 30° C. than room temperature), or humidity (i.e. less than 45%, 35%, or 25% relative humidity).

Amorphous L-dT

An amorphous and hygroscopic form of beta-L-2'-deoxythymidine is also disclosed that can be distinguished from crystalline beta-L-2'-deoxythymidine by Infra-Red and Raman spectroscopy, X-ray powder diffraction patterns, thermal properties, and methods of manufacture. The amorphous phase of beta-L-2'-deoxythymidine exhibits significant hygroscopicity and improved solubility when compared to crystalline beta-L-2'-deoxythymidine, a fact which could result in enhanced bioavailability in vivo. This form of beta-L-2'-deoxythymidine can be used in the manufacture of other forms of beta-L-2'-deoxythymidine, or in pharmaceutical compositions. Particularly preferred uses of this form are the treatment of hepatitis B.

Figure 1:
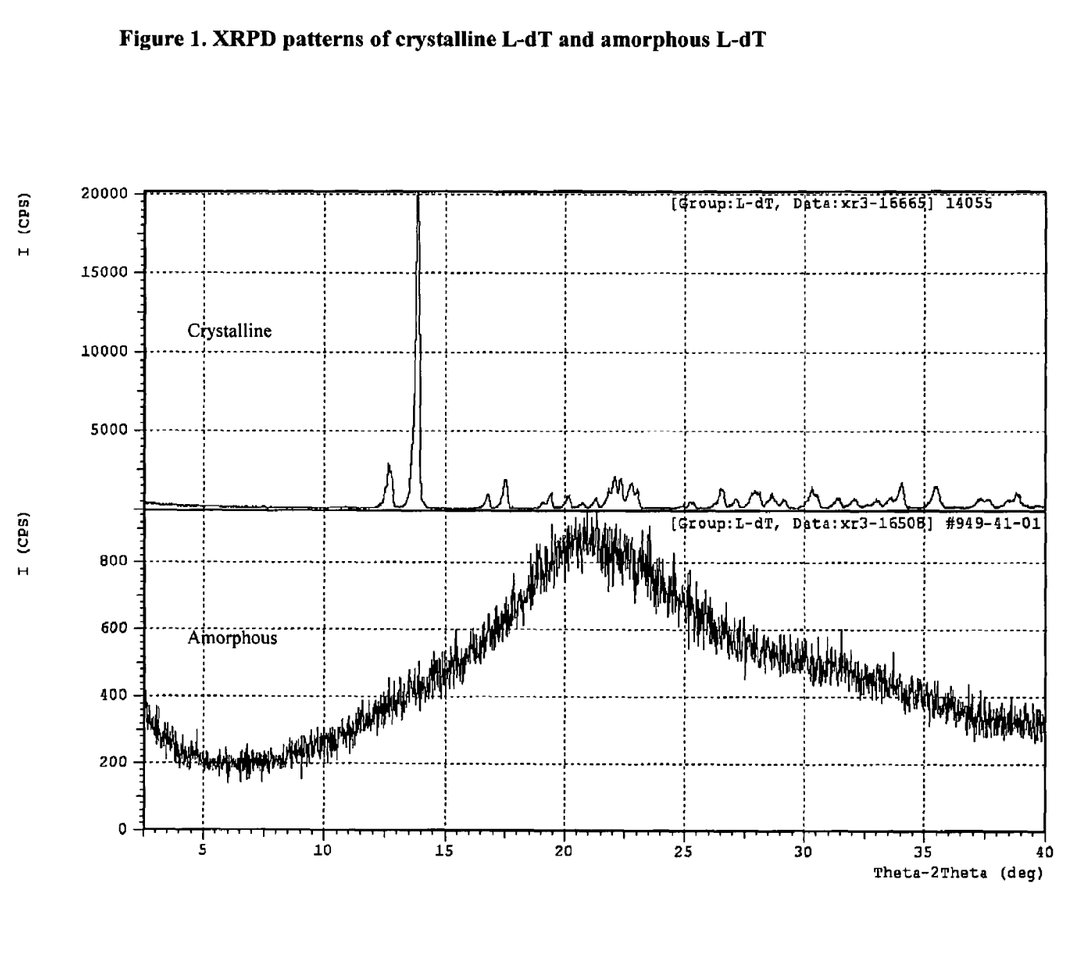
FIG. 1 is a XRPD ("X-ray powder diffraction") pattern of crystalline beta-L-2'-deoxythymidine and amorphous beta-L-2'-deoxythymidine.
Figure 2:
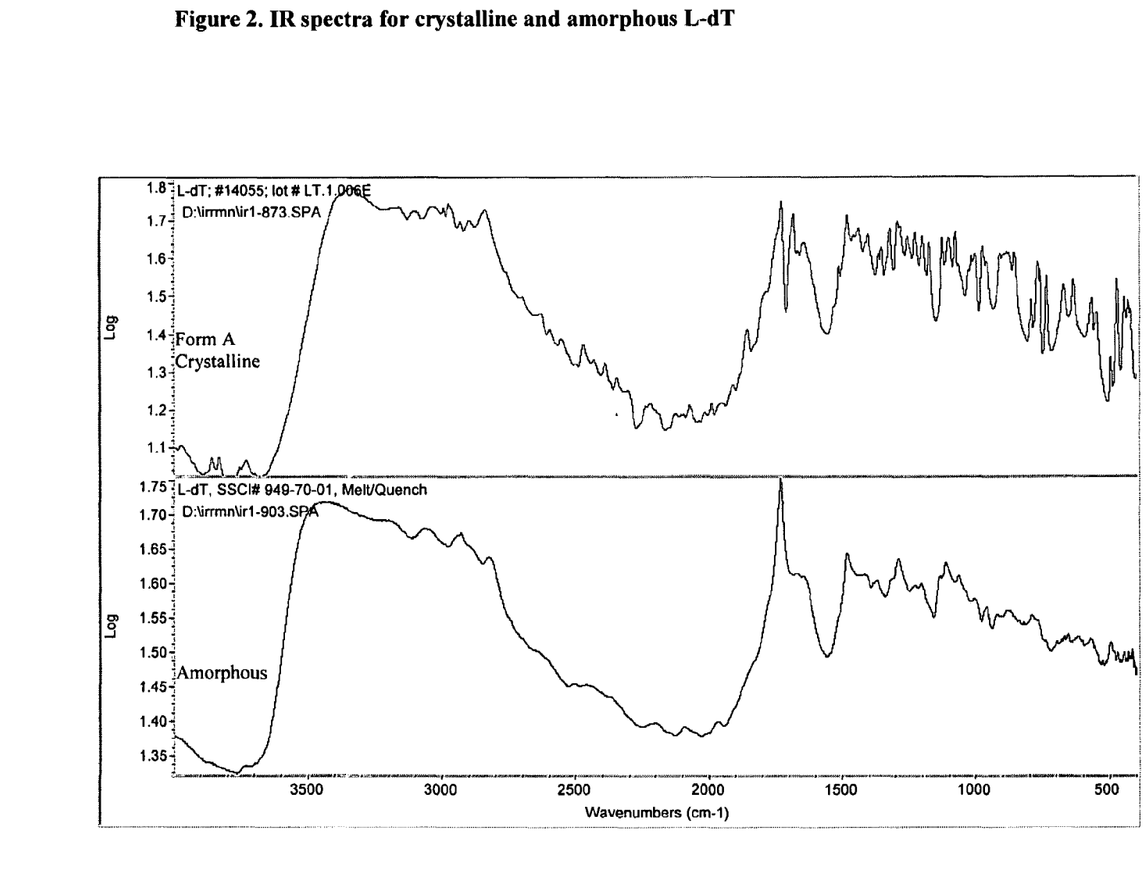
FIG. 2 is a graphical depiction of the Infra-Red (1R) spectra of crystalline beta-L-2'-deoxythymidine and amorphous beta-L-2'-deoxythymidine.
Figure 3:
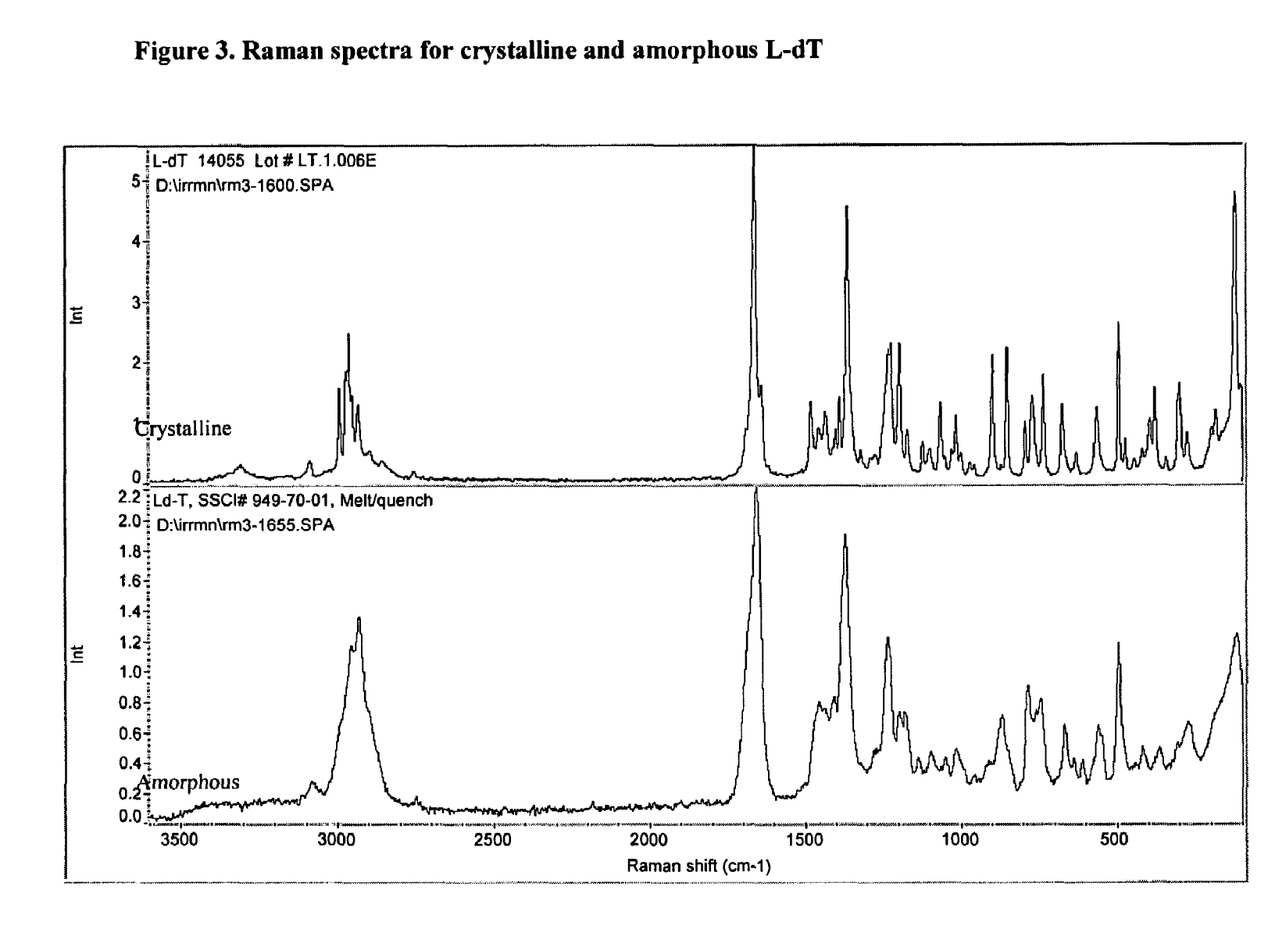
FIG. 3 is a graphical depiction of the Raman spectra of crystalline beta-L-2'-deoxythymidine and amorphous beta-L-2'-deoxythymidine.
Figure 5:
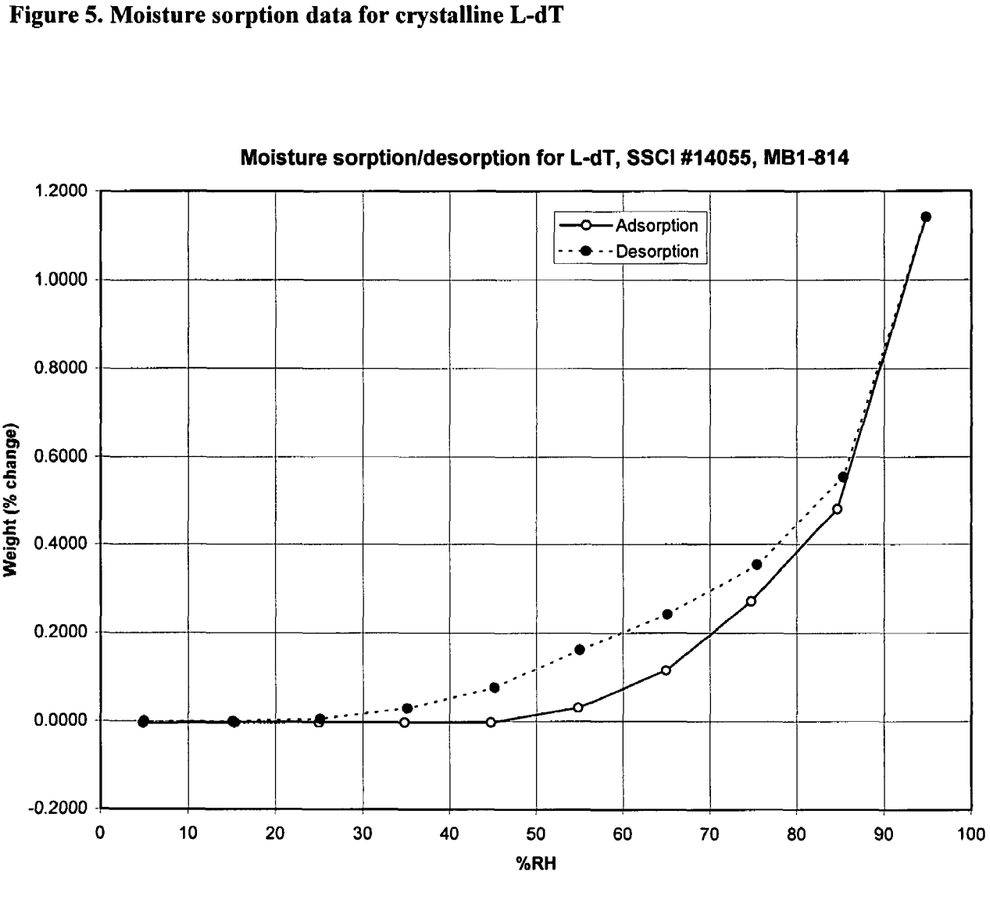
FIG. 5 depicts in graphical form the moisture sorption and desorption data for crystalline beta-L-2'-deoxythymidine.
Figure 6:
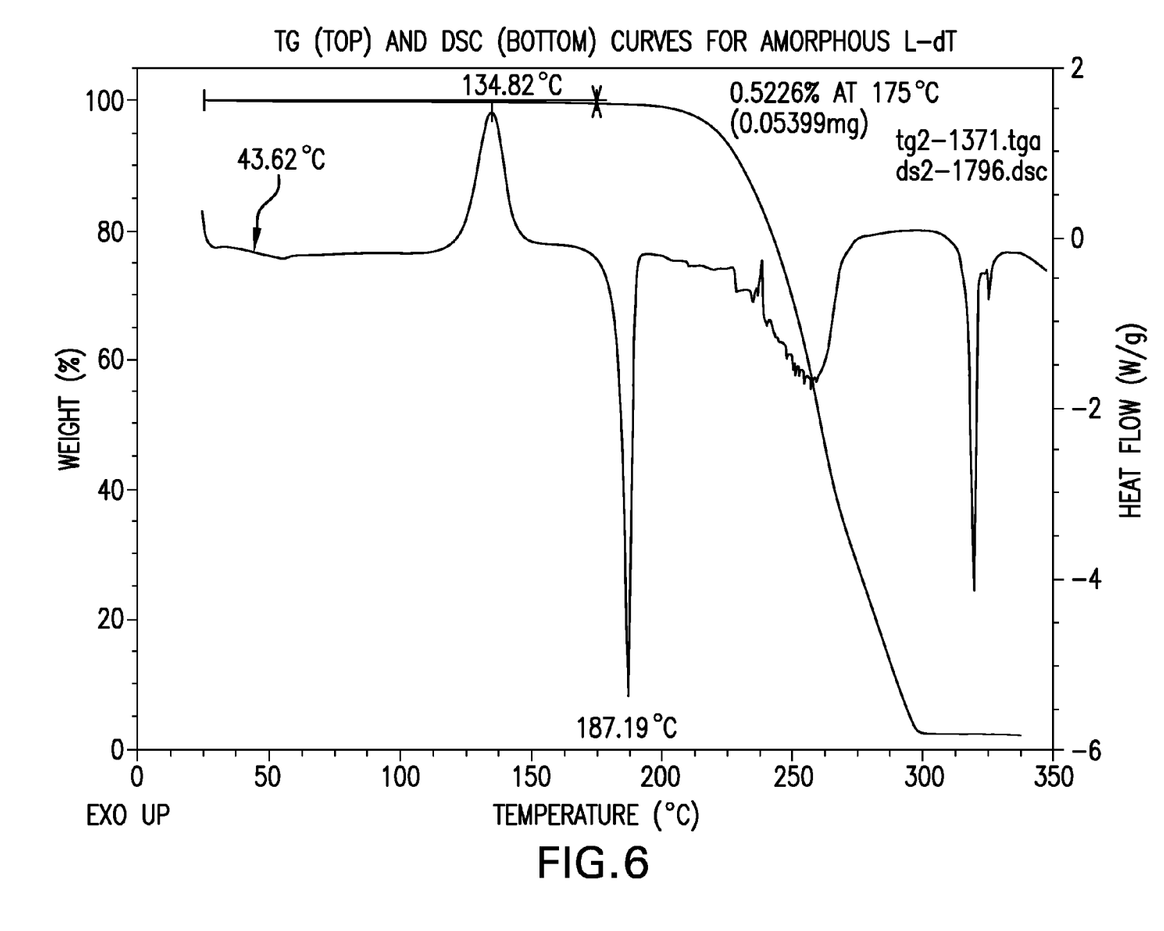
FIG. 6 is a graphical depiction of a TGA scan of amorphous beta-L-2'-deoxythymidine superimposed over a typical DSC thermogram of the same amorphous beta-L-2'-deoxythymidine, with an endotherm at 187.19° C.
Figure 7:
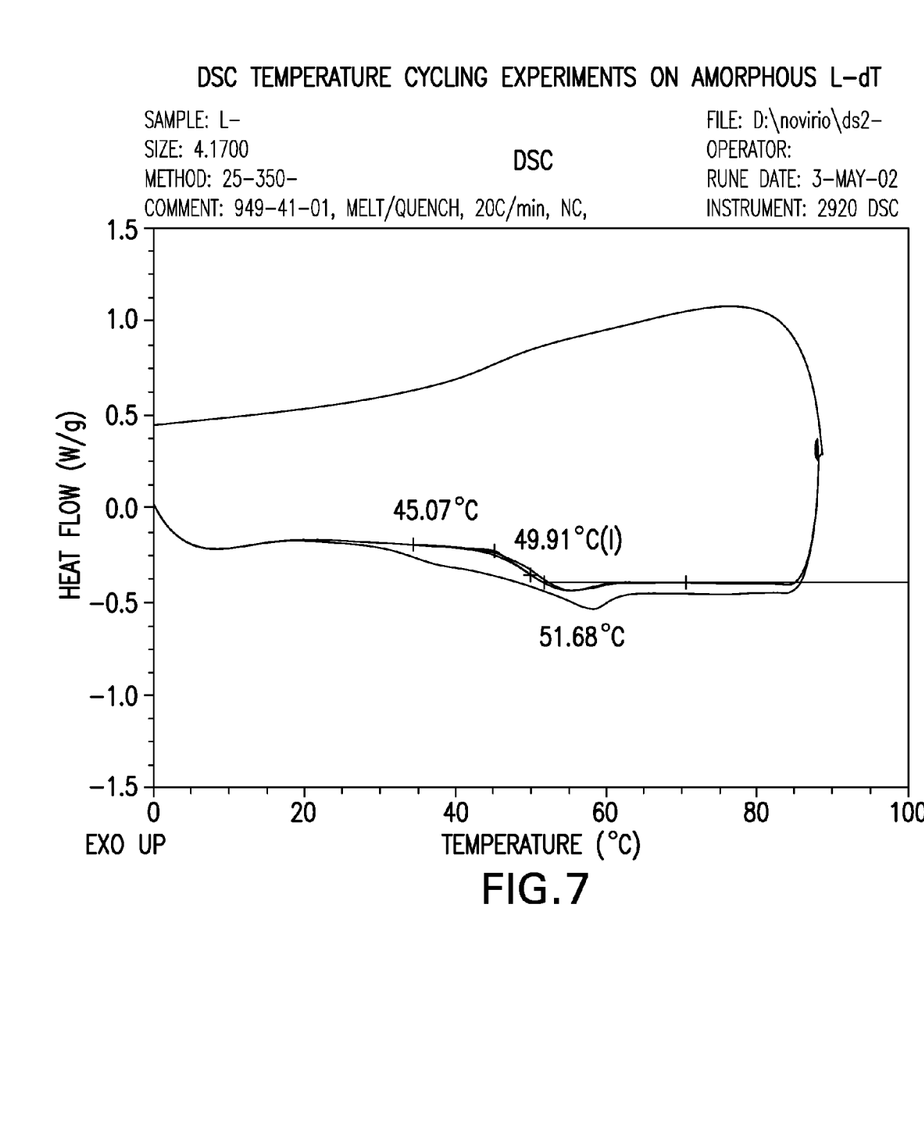
FIG. 7 depicts a DSC thermogram obtained from temperature cycling experiments on amorphous beta-L-2'-deoxythymidine.
Figure 8:
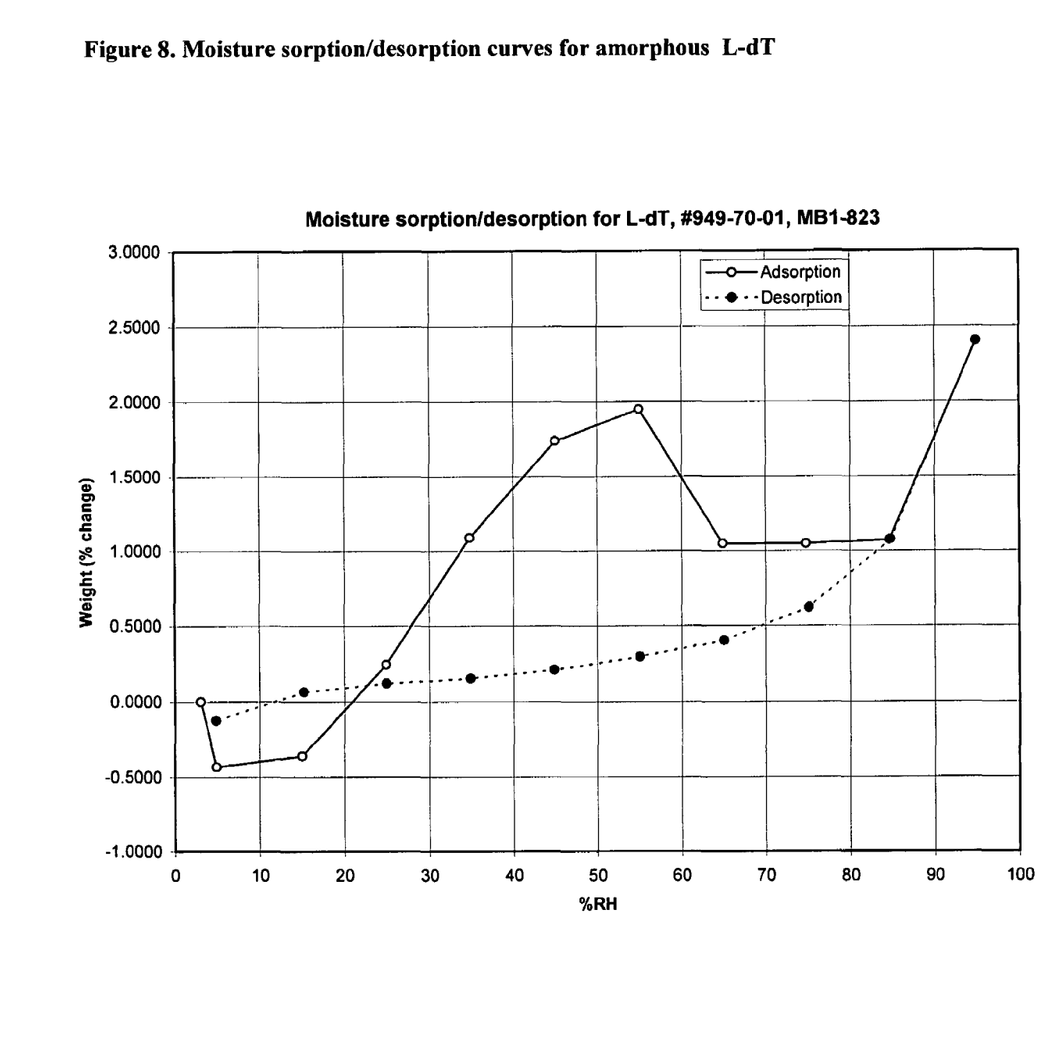
FIG. 8 depicts in graphical form the moisture sorption and desorption data for amorphous beta-L-2'-deoxythymidine.

The amorphous and hygroscopic form of beta-L-2'-deoxythymidine is characterized by the IR and Raman spectra in FIGS. 2 and 3, the TGA and DSC curves in FIG. 6, the DSC temperature cycling characteristics shown in FIG. 7, the moisture sorption data shown in FIG. 8, and/or the X-ray powder diffraction pattern in FIG. 1. This form should be contrasted with crystalline beta-L-2'-deoxythymidine, which can be characterized by the IR and Raman spectra in FIGS. 2 and 3, the TGA and DSC curves in FIG. 4, the moisture sorption data shown in FIG. 5, and/or the X-ray powder diffraction pattern shown in FIG. 1. Amorphous and crystalline forms of beta-L-2'-deoxythymidine are further characterized in the Examples contained herein.

Thus, the invention further provides:
  a) an amorphous and hygroscopic phase of beta-L-2'-deoxythymidine, as characterized by X-ray powder diffraction analysis, physical properties, and methods of manufacture;
  b) processes for making an amorphous and hygroscopic phase of beta-L-2'-deoxythymidine;
  c) therapeutic and/or pharmaceutical compositions of the amorphous and hygroscopic phase of beta-L-2'-deoxythymidine, optionally in the presence of a pharmaceutically acceptable carrier; and
  d) novel therapeutic uses for the amorphous and hygroscopic phase of beta-L-2'-deoxythymidine, especially in the treatment of viral diseases such as hepatitis B.

Amorphous beta-L-2'-deoxythymidine is obtained when melted beta-L-2'-deoxythymidine is rapidly quenched to below about 40 or 50° C. A DSC temperature cycling thermogram of amorphous beta-L-2'-deoxythymidine is presented in FIG. 7, which shows that the glass transition temperature for this phase is about 50° C.

Low temperatures and low levels of humidity are preferably observed when storing amorphous beta-L-2'-deoxythymidine. For example, it is preferred to store amorphous beta-L-2'-deoxythymidine at temperatures below 50, 40, 30, 20, 10, or 0° C. Moreover, it is preferred to store the amorphous beta-L-2'-deoxythymidine at relative humidities of less than 25%, 20%, 15%, 10%, or 5%.

In another embodiment, the invention provides amorphous beta-L-2'-deoxythymidine in substantially pure form i.e., in the absence of crystalline beta-L-2'-deoxythymidine. In still another embodiment the invention provides a pharmaceutical composition that comprises amorphous beta-L-2'-deoxythymidine, further comprising a pharmaceutically acceptable carrier.

Analytical Methods of Assuring the Purity of Crystalline L-dT

In view of the stability issues surrounding amorphous beta-L-2'-deoxythymidine, it is very important to ensure during the manufacturing process that batches of crystalline L-dT are not inadvertently contaminated by the amorphous form. Thus, other embodiments of the present invention relate to methods of detecting crystalline beta-L-2'-deoxythymidine contaminated by the amorphous form of beta-L-2'-deoxythymidine, and to methods of manufacturing crystalline beta-L-2'-deoxythymidine that is substantially free of amorphous beta-L-2'-deoxythymidine. As can be seen by a comparison of FIGS. 2 and 3, crystalline and amorphous beta-L-2'-deoxythymidine can each be characterized by IR and Raman spectrometry, and the two forms can be distinguished by peak broadening that occurs from the crystalline to the amorphous form. These peak broadenings are observed between 2200–2600, 1600–1800, 1000–1500, or 500–1000 cm$^{-1}$ in an IR spectra, and between 2800–3200, 1600–1675, 1300–1500, or 700–900 in a Raman spectra.

Therefore, in various embodiments the invention provides a method of detecting amorphous contamination of beta-L-2'-deoxythymidine, or distinguishing between crystalline and amorphous beta-L-2'-deoxythymidine, comprising:

subjecting a material that contains beta-L-2'-deoxythymidine to IR spectrometry; and evaluating breadth of peaks displayed between 2200–2600, 1600–1800, 1000–1500, or 500–1000 cm$^{-1}$ by reference to a known IR spectra for crystalline beta-L-2'-deoxythymidine.

In other embodiments the invention provides a method of detecting amorphous contamination of beta-L-2'-deoxythymidine, or distinguishing between crystalline and amorphous beta-L-2'-deoxythymidine, comprising:

subjecting a material that contains beta-L-2'-deoxythymidine to Raman spectrometry; and evaluating the breadth of peaks displayed between 2800–3200, 1600–1675, 1300–1500, or 700–900 cm$^{-1}$ by reference to a known Raman spectra for crystalline beta-L-2'-deoxythymidine.

In still other embodiments the invention relates to the manufacture of pharmaceutical compositions of crystalline beta-L-2'-deoxythymidine substantially in the absence of the amorphous form. Thus, the invention provides a method of manufacturing pharmaceutical formulations of crystalline beta-L-2'-deoxythymidine comprising:

crystallizing two or more batches of beta-L-2'-deoxythymidine from solution;

subjecting the batches to IR spectrometry;

selecting for further processing the batches that do not display significant breadth of peaks (i.e. breadth consistent with the presence of amorphous L-dT) between 2200–2600, 1600–1800, 1000–1500, or 500–1000 cm$^{-1}$ from a known IR spectra for crystalline beta-L-2'-deoxythymidine; and formulating said selected batches into pharmaceutical formulations of beta-L-2'-deoxythymidine.

In another embodiment, the invention provides a method of manufacturing pharmaceutical formulations of crystalline beta-L-2'-deoxythymidine comprising:

crystallizing two or more batches of beta-L-2'-deoxythymidine from solution;

subjecting the batches to Raman spectrometry;

selecting for further processing the batches do not display significant breadth of peaks (i.e. breadth consistent with the presence of amorphous L-dT) between 2800–3200, 1600–1675, 1300–1500, or 700–900 cm$^{-1}$ from a known Raman spectra of crystalline beta-L-2'-deoxythymidine; and formulating said selected batches into pharmaceutical formulations of beta-L-2'-deoxythymidine.

EXAMPLES

Example 1 -- Stereoselective Chemical synthesis of beta-L-2'-deoxythymidine

3',5'-Di-O-benzoyl-2'-deoxy-5-iodo-β-L-uridine (7)

A mixture of compound 5 (105.8 g, 0.242 mol), iodine (76.8 g), CAN (66.4 g) and acetonitrile (2550 ml) was stirred at 80° C. for 3 h then the reaction mixture was cooled at room temperature leading to crystallization of compound 7 (86.6 g, 63.5%); m. p. 192–194° C.; $^1$H NMR (DMSO) δ ppm 0.8.34 (s, 1H, NH), 8.2–7.2 (m, 11H,2 C$_6$H$_5$CO, H-6), 6.31 (q, 1H, H-1', J=5.5 Hz and J=8.7 Hz), 5.5 (m, 1H, H-3'), 4.7 (m, 2H, H-5', H-5''), 4.5 (m, 1H, H-4'), 2.7 (m, 1H, H-2'), 2.3 (m, 1H, H-2''); FAB<0, (GT) m/e 561 (M–H)$^-$, 237 (B)$^-$; FAB>0 (GT) 563 (M+H)$^+$; [α]$_D^{20}$+39.05 (c=1.05 in DMSO); UV (EtOH 95) ν$_{max}$=281 nm (ε=9000), ν$_{min}$=254 nm (ε=4000), ν$_{max}$=229 nm (ε=31000); Anal. Calcd for C$_{23}$H$_{19}$IN$_2$O$_7$: C, 49.13H, 3.41 N, 4.98 I, 22.57. Found: C, 49.31H, 3.53 N, 5.05 I, 22.36.

Reagents:

Iodine: Fluka, 99.8%, ref 57650

Cerium ammonium nitrate (CAN): Aldrich, >98.5%, ref 21,547–3

3',5'-Di-O-benzoyl-2'-deoxy-3-N-toluoyl-β-L-thymidine (9)

To a solution of compound 7 (86.6 g, 0.154 mol) in anhydrous pyridine (1530 ml) containing N-ethyldiisopropylamine (53.6 ml) was added, portionwise at 0° C., p-toluoyl chloride (40.6 ml). The reaction mixture was stirred for 2 h at room temperature, then water was added to stop the reaction and the reaction mixture was extracted with methylene chloride. The organic phase was washed with water, dried over sodium sulfate and evaporated to dryness to give crude 3',5'-di-O-benzoyl-2'-deoxy-3-N-toluoyl-5-iodo-β-L-uridine (§) which can be used for the next step without further purification.

A solution of the crude mixture 8, palladium acetate (3.44 g), triphenylphosphine (8.0 g) in N-methylpyrrolidinone (1375 ml) with triethylamine (4.3 ml) was stirred at room temperature for 45 min. Then, tetramethyltin (42.4 ml) was added dropwise at 0° C. under argon. After stirring at 100–110° C. overnight, the reaction mixture was poured into water and extracted with diethyl ether. The organic solution was dried over sodium sulfate and concentrated under reduced pressure. The residue was purified by a silica gel column chromatography [eluant: stepwise gradient of ethyl acetate (0–10%) in toluene] to give compound 9 as a foam (42.3 g, 48.3% for the 2 steps). $^1$H NMR (DMSO) δ ppm 0.8.3–7.2 (m, 15H, 2 $C_6H_5CO$, 1 $CH_3C_6H_4CO$, H-6), 6.29 (t, 1H, H-1', J=7.0Hz), 5.7 (m, 1H, H-3'), 4.7–4.5 (m, 3H, H-5', H-5", H-4'), 2.7–2.6 (m, 2H, H-2'H-2"); FAB<0, (GT) m/e 567 (M−H)$^-$, 449 (M-$CH_3C_6H_4CO$)$^-$, 243 (B)$^-$, 121 ($C_6H_5COO$)$^-$; FAB>0 (GT) 1137 (2M+H)$^+$, 569 (M+H)$^+$, 325 (M−B)$^-$, 245 (B+2H)$^+$, 119 ($CH_3C_6H_5CO$)$^+$.

Reagents:
p-Toluoyl chloride, Aldrich, 98%, ref 10,663–1
Diisopropylethylamine: Aldrich, >99.5%, ref 38,764–9
N-methylpyrrolidinone: Aldrich, >99%, ref 44,377–8
Palladium acetate: Aldrich, >99.98%, ref 37,987–5
Triphenylphosphine: Fluka, >97%, ref 93092
Tetramethyltin: Aldrich, >99%, ref 14,647–1

2'-Deoxy-β-L-thymidine

A solution of compound 9 (42.3 g, 0.074 mol) in methanol saturated with ammonia (1850 ml) was stirred at room temperature for two days. After evaporation of the solvent, the residue was diluted with water and washed several times with ethyl acetate. The aqueous layer was separated, evaporated under reduced pressure and the residue was purified by a silica gel column chromatography [eluant: stepwise gradient of methanol (0–10%) in methylene chloride] to give pure 2'-deoxy-β-L-thymidine (11.62 g, 64.8%) which was crystallized from ethanol; m.p. 185–188° C.; $^1$H NMR (DMSO) δ ppm 11.3 (s, 1H, NH), 7.70 (s, 1H, H-6), 6.2 (pt, 1H, H-1'), 5.24 (d, 1H, OH-3', J=4.2 Hz), 5.08 (t, 1H, OH-5', J=5.1 Hz), 4.2 (m, 1H, H-3'), 3.7 (m, 1H, H-4'), 3.5–3.6 (m, 2H, H-5', H-5"), 2.1–2.0 (m, 2H, H-2', H-2"); FAB<0, (GT) m/e 483 (2M−H)$^-$, 349 (M+T−H)$^-$, 241 (M−H)$^-$, 125 (B)$^-$; FAB>0 (GT) 243 (M+H)$^+$, 127 (B+2H)$^+$;)$^+$; $[α]_D^{20}$ −13.0 (c=1.0 in DMSO); UV (pH 1) $v_{max}$=267 nm (ϵ=9700), $v_{min}$=234 nm (ϵ=2000).

Reagent:

Methanolic ammonia: previously saturated at −5° C., tightly stoppered, and kept in a freezer.

Example 2

Characterization of Physical Forms of L-dT

Experimental Methods

Crystallization Studies

A weighed sample of L-dT (usually 20–30 mg) was treated with aliquots of the test solvent. Solvents were either reagent or HPLC grade. The aliquots were usually 100 μL or 500 μL. Between additions the mixture was sonicated. When the solids dissolved, as judged by visual inspection, the solution was filtered, then left in an open vial under ambient conditions (fast evaporation). The procedure was repeated, and the resulting solution was left under ambient conditions in a vial with aluminum foil containing pinholes (slow evaporation). Samples were also generated by filtering a warm solution of L-dT into a cold antisolvent (cold precipitation).

Solubilities were estimated from these experiments based on the total solvent used to give a solution. Note that actual solubilities may be greater than those calculated because of the use of too-large solvent aliquots or a slow rate of dissolution. If the dissolution did not occur during the experiment the solubility is expressed as "less than." If the solid dissolved before the whole aliquot of solvent was added the solubility is listed as "greater than."

The solid was also dissolved in a test solvent at an elevated temperature (either 45 or 60° C.). The resulting solution was rapidly filtered into a vial kept on the same hotplate. The heat source was then turned off and the hotplate and vial were allowed to cool to room temperature (slow cool). The vial was then allowed to stand at ambient temperature overnight. The presence or absence of undissolved solids was noted; if there were no solids present, or an amount of solid judged too small for XRPD analysis, the vial was placed in a refrigerator overnight. Again the presence or absence of undissolved solids was noted and, if there were none, the vial was placed in a freezer overnight. Solids were removed by filtration and allowed to dry in the air.

Slurry experiments were carried out by making saturated solutions containing excess solid. The slurries were agitated at ambient temperature. The insoluble solids were recovered by filtration. Crystallizations using antisolvent addition were also performed. Solid was dissolved in a solvent and filtered into an antisolvent at either 0° C. or −78° C. If no solids immediately formed, the samples were either left to stand under ambient conditions and/or the solvent was removed by rotary evaporation. Any solids formed were removed by filtration and air-dried. Vapor diffusion experiments involved placing a saturated solution of L-dT in a vial. The vial was placed in a larger vial containing an antisolvent which was then sealed and kept at ambient temperature. Samples were also generated by cooling of a melt of L-dT to room temperature and also lyophilization using water.

All samples generated as described above were air-dried and analyzed by X-ray powder diffraction (XRPD).

X-Ray Powder Diffraction

X-ray powder diffraction (XRPD) analyses were performed using a Shimadzu XRD-6000 X-ray powder diffractometer using Cu Kα radiation. The instrument is equipped with a fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40 '2θ was used. A silicon standard was analyzed to check the instrument alignment. Data were collected and analyzed using XRD-6000 v. 4.1. Samples were prepared for analysis by placing them in a silicon sample holder or aluminum holder with silicon insert.

Characteristic powder X-ray diffraction pattern peak positions are reported for crystalline forms in terms of the angular positions (two theta) within an allowable variability of plus or minus 0.1°. This allowable variability is specified by the US Pharmacopeia, pages 1843–1844 (1995). The variability of plus or minus 0.1° is intended to be used when comparing two powder X-ray diffraction patterns. In practice, if a diffraction pattern peak from one pattern is assigned a range of angular positions (two theta) which is a measured peak position plus or minus 0.1° and a diffraction pattern peak from the other pattern is assigned a range of angular positions (two theta) which is the measured peak position plus or minus 0.1° and if those ranges of peak positions overlap, then the two peaks are considered to have the same angular position (two theta). For example, if a diffraction pattern peak from one pattern is determined to have a peak position of 5.20°, for comparison purposes the allowable variability allows the peak to be assigned a position in the range of 5.10°–5.30°. If a comparison peak from the other diffraction pattern is determined to have a peak position of 5.35°, for comparison purposes the allowable variability allows the peak to be assigned a position in the range of 5.25°–5.45°. Because there is overlap between the two ranges of peak positions, the two peaks being compared are considered to have the same angular position (two theta).

Thermal Analysis

Thermogravimetric (TG) analyses were performed using a TA Instruments 2050 or 2950 thermogravimetric analyzer. Each sample was placed in an aluminum sample pan and inserted into the TG furnace. Samples were first equilibrated at 25° C., then heated under nitrogen at a rate of 10° C./min, up to a final temperature of 350° C. Nickel and Alumel™ were used as the calibration standards.

Differential scanning calorimetry (DSC) was performed using a TA Instruments differential scanning calorimeter 2920. The sample was placed into an aluminum DSC pan, and the weight accurately recorded. The pan was covered with a lid and left uncrimped. Each sample was equilibrated at 25° C. and heated under a nitrogen purge at a rate of 10° C./min, up to a final temperature of 350° C. For studies of the glass transition temperature ($T_g$) of the amorphous material, the sample was heated at a rate of 20° C./min, up to 90° C. and held there for 3 minutes. The sample was then allowed to cool and equilibrate at 0° C. The sample was again heated at a rate of 20° C./min, up to 90° C., held there for 3 minutes, and then cooled to 0° C. The sample was then heated at 20° C./min up to a final temperature of 225° C. Indium metal was used as the calibration standard.

Hot stage microscopy was performed using a Linkam hot stage (model FTIR 600) mounted on a Leica DMLP microscope equipped with a Sony DXC-970MD 3CCD camera for collecting images. A 10× objective was used with cross polarizers to view samples. Samples were placed on a glass coverslip. A coverslip was then placed over the sample. Each sample was visually observed as the stage was heated. Images were captured using Linksys version 2.27 (Linkam). The hot stage was calibrated using USP melting point standards.

Spectroscopy

Infrared spectra were acquired on a Magna-IR 560®/or 860® Fourier transform infrared (FT-IR) spectrophotometer (Thermo Nicolet) equipped with an Ever-Glo mid/far IR source, potassium bromide (KBr) beamsplitter, and a deuterated triglycine sulfate (DTGS) detector. A diffuse reflectance accessory (the Collector™, Thermo Spectra-Tech) was used for sampling. Each spectrum represents 256 co-added scans collected at a spectral resolution of 4 cm$^{-1}$. Sample preparation consisted of placing the sample into a 3-mm diameter cup and leveling the material with a frosted glass slide. A background data set was acquired with an alignment mirror in place. A Log 1/R(R=reflectance) spectrum was acquired by taking a ratio of these two data sets against each other. Wavelength calibration was performed using polystyrene.

FT-Raman spectra were acquired on an FT-Raman 960 spectrometer (Thermo Nicolet). This spectrometer uses an excitation wavelength of 1064 nm. Approximately 0.5 W of Nd:YVO$_4$ laser power was used to irradiate the sample. The Raman spectra were measured with an indium gallium arsenide (InGaAs) detector. The samples were prepared for analysis by placing the material in a glass tube and positioning the tube in a gold-coated tube holder in the accessory. A total of 256 sample scans were collected from 100–3600 cm$^{-1}$ at a spectral resolution of 4 cm$^{-1}$, using Happ-Genzel apodization. Wavelength calibration was performed using sulfur and cyclohexane.

Moisture Sorption/Desorption

Moisture sorption/desorption data were collected on a VTI SGA-100 Vapor Sorption Analyzer. Sorption and desorption data were collected over a range of 5% to 95% relative humidity (RH) at 10% RH intervals under a nitrogen purge. Samples were not dried prior to analysis. Equilibrium criteria used for analysis were less than 0.0100% weight change in 5 minutes, with a maximum equilibration time of 3 hours if the weight criterion was not met. Data were not corrected for the initial moisture content of the samples. NaCl and PVP were used as calibration standards.

RESULTS

Approximate Solubilities

Approximate solubilities of L-dT in various solvents at ambient temperature were determined during the crystalline screen, and are summarized in Table 1. L-dT was found to be most soluble in 1:1 THF:water (127 mg/mL), followed by N,N-dimethylformamide (72 mg/mL), 1:1 methanol:water (58 mg/mL), 4:1 acetone:water (51 mg/mL), water (32 mg/mL), 1,1,1,3,3,3-hexafluoro-2-propanol (22 mg/mL), methanol (11 mg/mL), 2,2,2-trifluoroethanol (8 mg/mL) and EtOH (>4 mg/mL). L-dT is sparingly soluble in acetone, acetonitrile, ethyl acetate, diethyl ether, isopropanol, methylene chloride, and toluene Crystallization Studies Crystallization studies were also carried out to generate different solid forms of L-dT. The technique involved generation of solid L-dT under a variety of conditions and characterization of the resulting samples by XRPD. The experiments performed are summarized in Tables 2 and 3. One distinct crystalline XRPD pattern was found, termed crystalline L-dT, as well as an amorphous form. Amorphous material was generated by quenching a melt of the material on a cold countertop or lyophilization from aqueous solution. Many of the generated samples exhibited preferred orientation. Preferred orientation can affect peak intensities, but not peak positions, in XRPD patterns. The sections below summarize the characterization of the crystalline and amorphous materials.

Characterization of Crystal Form

The XRPD pattern of the initial material received for the crystallization screen is shown in FIG. 1, and was termed representative of crystalline L-dT. Almost all of the crystallizations performed during the course of the screen resulted in crystalline L-dT material. The IR and Raman spectra for crystalline L-dT are shown in FIGS. 2 and 3, respectively.

Figure 4:
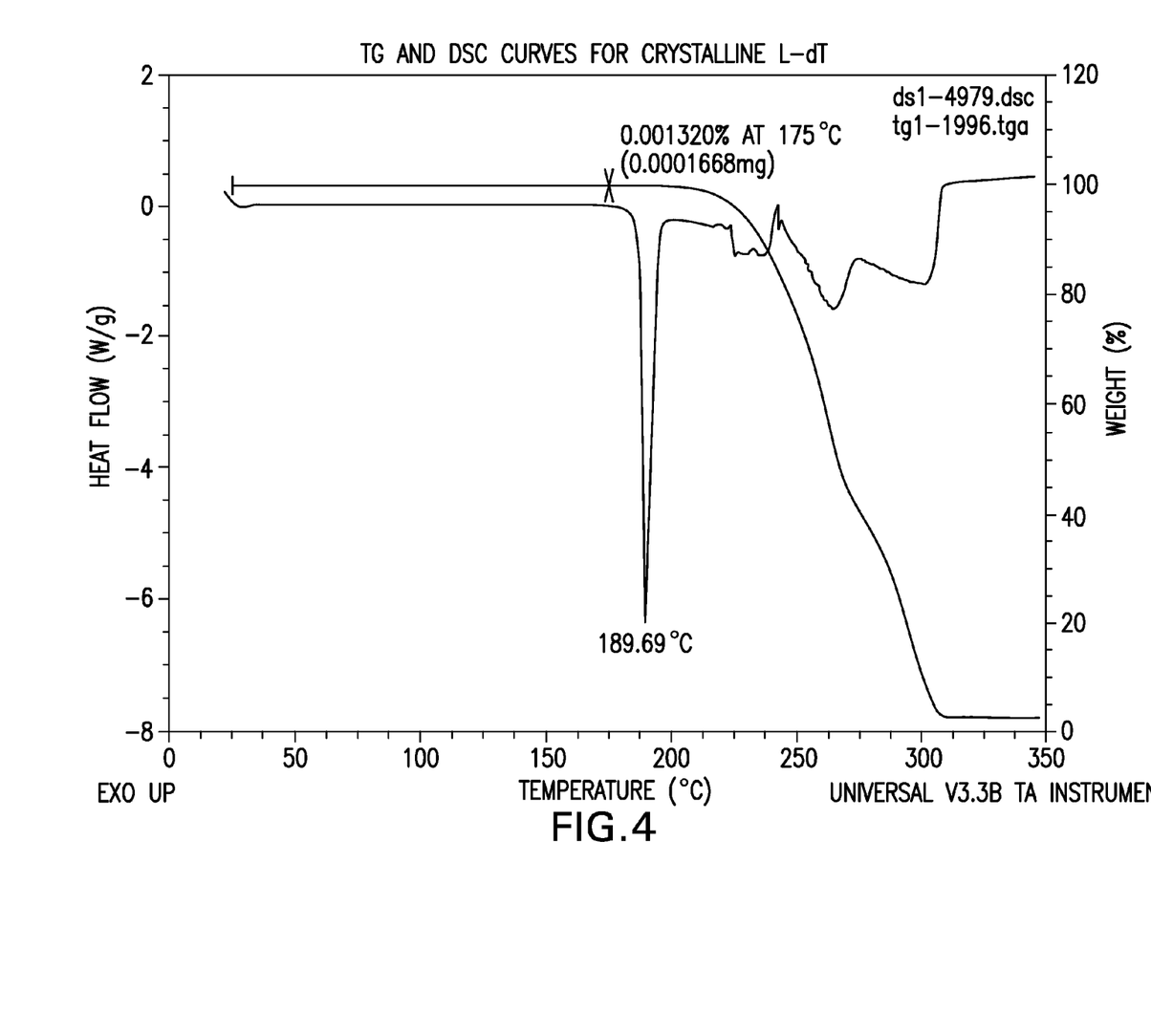
FIG. 4 is a graphical depiction of a TGA ("thermogravimetric analysis") scan of crystalline beta-L-2'-deoxythymidine superimposed over a typical DSC ("differential scanning calorimetry") thermogram of the same crystalline beta-L-2'-deoxythymidine, with an endotherm at 189.69° C.

The thermal data for crystalline L-dT is shown in FIG. 4 and listed in Table 4. The TG curve displays minimal weight loss up to 175° C., indicating an unsolvated material. The DSC curve displays an endotherm at 190° C. The moisture sorption data for crystalline L-dT is shown in FIG. 5 and summarized in Table 5. The material gains a relatively small amount of weight up to 45% RH, but above this point the material gains weight up to a total of 1.1% at 95% RH. All of this weight is lost upon lowering the relative humidity to 5% RH.

Characterization of Amorphous Form

Amorphous material was prepared by quenching a melt of the material to room temperature or by lyophilization from aqueous solutions. The IR and Raman spectra of amorphous are shown in FIG. 2 and FIG. 3, respectively. The IR spectra for the amorphous material differs from the crystalline material in that the peaks from the amorphous material are broader and vary in shape between 1500–1900 cm$^{-1}$. The peaks in the Raman spectrum of the amorphous material also are broader than those seen for the crystalline material; however, the amorphous Raman spectrum displays significant peak shifts around 2800–3200, 1600–1675, 1300–1500, and 700–900 cm$^{-1}$.

The thermal data for the amorphous is shown in FIG. 6. The TG curve shows a 0.5% weight loss up to 175° C. The material displays an exothermic event at about 135° C., which is likely a crystallization, followed by a melting endotherm at about 187° C. A DSC temperature cycling experiment, shown in FIG. 7, demonstrates that the glass transition temperature for the amorphous material is ~50° C.

The moisture sorption data for amorphous L-dT is shown in FIG. 8. The material loses ~0.4% of its weight upon equilibration at about 5% RH, and gains ~2.3% up to about 55% RH. Above this point, the material loses some of this weight and continues to gain weight above about 85% RH. The material loses almost all of this weight upon lowering the relative humidity from about 95% RH to about 5% RH. The XRPD pattern of the material after the experiment matches that of crystalline L-dT. It is likely that the sudden weight drop above about 55% RH is indicative of a recrystallization and the concomittant loss of water.

TABLE 1

Approximate Solubilities of crystalline L-dT

| Solvent | Solubility (mg/mL)[a] |
|---|---|
| acetone | <4 |
| acetone:water (4:1) | 51 |
| acetonitrile (ACN) | <4 |
| dichloromethane | <3 |
| N,N-dimethylformamide (DMF) | 72 |
| ethanol (EtOH) | >3.6* |
| ethyl acetate (EtOAc) | <4 |
| ethyl ether | <3 |
| 1,1,1,3,3,3-hexafluoroisopropanol | 22 |
| hexane | <4 |
| isopropanol (IPA) | <3 |
| methanol (MeOH) | 11 |
| MeOH:water (1:1) | 58 |
| tetrahydrofuran (THF) | 4 |
| THF:water (1:1) | 127 |
| toluene | <4 |
| 2,2,2-trifluoroethanol | 8 |
| water | 32 |

[a]Solubilities are calculated based on the total solvent used to give a solution; actual solubilities may be greater because of the volume of the solvent portions utilized or a slow rate of dissolution. If a clear solution was not obtained the values for the solubilities are listed as "less than." If the solid dissolved before the whole aliquot of solvent was added the solubility is listed as '"greater than." Values are rounded to the nearest mg/mL.
*after 2 hours, all solid was dissolved.

TABLE 2

Crystallization Screen of L-dT

| Solvent | Conditions[a] | Habit | XRPD Results[b] |
|---|---|---|---|
| acetone | slurry | small white aciculars | crystalline |
| acetone | 1 day slurry (50° C.) | needles | crystalline |
| acetone:water (4:1) | FE | unknown | crystalline |
| | 1 day slurry (50° C.) | needles | crystalline |
| acetonitrile | slurry | small white aciculars | crystalline |
| | 1 day slurry (50° C.) | needles | crystalline |
| dichloromethane | slurry | small white aciculars | crystalline |
| diethyl ether | slurry | small white aciculars | crystalline |
| N,N-dimethyl-formamide (DMF) | FE | white chunks | crystalline |
| | SE | white needles, chunks | crystalline (PO) |
| | SC (60° C.) | no solid | — |
| ethanol | FE | white flakes, chunks | crystalline |
| | SE | clear aciculars | crystalline |
| | SC (60° C.) | Unknown white solid | crystalline |
| | CC | white solid | crystalline |
| | 1 day slurry (50° C.) | needles | crystalline |
| ethyl acetate | slurry | small white plates | crystalline |
| hexaflurorisopropanol | FE | small white flakes | crystalline |
| | SE | white flakes | crystalline |
| | SC (60° C.) | no solid | — |
| | rotovap | white solid | crystalline |
| hexanes | slurry | small white aciculars | crystalline |
| isopropanol | slurry | white powder | crystalline |
| | 1 day slurry (50° C.) | needles | crystalline |
| methanol | FE | white needles | crystalline |
| | SE | white needles, flakes | crystalline |
| | SC (60° C.) | white chunks | crystalline |
| | CC | white solid | crystalline |
| | rotovap | white solid | crystalline |
| MeOH:water (1:1) | FE | needles | crystalline |
| | 1 day slurry (50° C.) | no solids | — |
| | | no solids | — |
| | CC freezer | | |

TABLE 2-continued

Crystallization Screen of L-dT

| Solvent | Conditions[a] | Habit | XRPD Results[b] |
|---|---|---|---|
| toluene | slurry | white powder | crystalline |
| tetrahydrofuran (THF) | FE | clumps of white fibers | crystalline |
| | SE | white aciculars | crystalline (PO) |
| | SC (60° C.) | white needles | crystalline |
| | CC | white solid | crystalline |
| | rotovap | white solid | crystalline |
| THF:Water (1:1) | FE | needles | crystalline |
| | 1 day slurry (50° C.) CC | no solids | — |
| | freezer | no solids | — |
| 2,2,2-trifluoroethanol | FE | white needles, flakes | crystalline |
| | SE | white needles | crystalline |
| | SC (60° C.) | no solid | — |
| | rotovap | white solid | crystalline |
| water | FE | unknown white solid | crystalline |
| | SE | clear aciculars | crystalline |
| | SC (60° C.) | no solid | — |
| | 1 day slurry (50° C.) | needles | crystalline |
| | freeze dry | white solid | crystalline |
| | freeze dry | fluffy white solid | amorphous |
| | freeze dry | — | crystalline |
| | melt/quench | clear solid | amorphous |
| | melt/quench | clear solid | crystalline + amorphous |
| | melt/quench | clear solid | amorphous |
| | melt/quench | clear solid | amorphous |
| | melt/quench | clear solid | amorphous |

[a]FE = fast evaporation; SE = slow evaporation; SC = slow cool, CC = crash cool, rotovap = rotary evaporator
[b]PO = preferred orientation; LC = low crystallinity; SS = small sample; IS = insufficient sample

TABLE 3

Cold Precipitation Crystallizations

| Solvent | Anti-solvent | Habit | XRPD Results |
|---|---|---|---|
| N,N-dimethylformamide | acetone | no solid | — |
| | toluene | white solid | crystalline |
| ethanol | acetone | no solid | — |
| | ethyl acetate | white solid | crystalline |
| methanol | acetone | no solid | — |
| | dichloromethane | white solid | crystalline |
| | diethyl ether | white solid | crystalline |
| tetrahydrofuran | acetone | no solid | — |
| | diethyl ether | white solid | crystalline |
| | hexanes | white solid | crystalline |
| water | acetone | no solid | — |
| | acetonitrile | no solid | — |
| | isopropanol | no solid | — |

*solid dissolved in solvent at 60° C., hot filtered into vial containing cold antisolvent (cooled in dry-ice/acetone slurry) None of these yielded solid immediately, solid formed after samples had been in freezer several days.

TABLE 4

Thermal Data for L-dT Forms

| Form | DSC Results (° C.)[a] | TG Results[b] |
|---|---|---|
| crystalline | endo 190 | <0.1 |
| amorphous | transition ~44, exo 135, endo 187 | 0.5 |
| amorphous | $T_g$ ~50 | — |

[a]maximum temperature reported; endo = endotherm; exo = exotherm; $T_g$ = glass transition
[b]percent volatiles measured at 175° C.

TABLE 5

Summary of Moisture Sorption/Desorption Data for For Crystalline L-dT Solid Forms

| Lot No. | Moisture Balance Results | XRPD Results |
|---|---|---|
| 1 | <0.1% weight loss at 5% RH<br>1.1% weight gain at 95% RH<br>1.1% loss from 95–5% RH | crystalline |
| 2 | −0.4% weight loss at 5% RH<br>2.8% weight gain at 95% RH<br>2.7% loss from 95–5% RH | crystalline |

PHARMACEUTICAL COMPOSITIONS

Humans suffering from viral diseases such as HBV can be treated by administering to the patient an effective amount of the forms of the compound of the present invention, or a pharmaceutically acceptable prodrug or salt thereof in the presence of a pharmaceutically acceptable carrier or diluent. The active materials can be administered by any appropriate route, for example, orally, parenterally, or intravenously, in liquid or solid form.

A preferred dose of the compound for HBV will be in the range from about 1 to 75 mg/kg, preferably 1 to 50 or 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in any suitable dosage form, including but not limited to one containing 7 to 3000 mg, preferably 70 to 1400 mg of active ingredient per unit dosage form. An oral dosage of 50–1000 mg is usually convenient.

Ideally the active ingredient should be administered to achieve peak plasma concentrations of the active compound of from about 0.2 to 70 μM, preferably about 1.0 to 10 μM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. Amorphous beta-L-2'-deoxythymidine.

2. Amorphous beta-L-2'-deoxythymidine in substantially pure form.

3. A substantially pure amorphous phase of beta-L-2'-deoxythymidine prepared by quench cooling the melted beta-L-2'-deoxythymidine.

4. A process of preparing substantially pure amorphous beta-L-2'-deoxythymidine comprising:
   a) melting a beta-L-2'-deoxythymidine, and
   b) quench cooling the melt to avoid recrystallization.

5. The process of claim 4 further comprising cooling the beta-L-2'-deoxythymidine to below about 50° C.

6. The process of claim 4 further comprising storing the amorphous beta-L-2'-deoxythymidine at a relative humidity below about 20%.

7. A pharmaceutical composition comprising the compound or composition of any one of claims 1–3, and a pharmaceutically acceptable carrier.

8. A method of treating hepatitis B virus comprising administering to a patient afflicted with the disease a treatment effective amount of the compound of any one of claims 1–3.

9. The amorphous beta-L-2'-deoxythymidine of claim 2, wherein the amorphous beta-L-2'-deoxythymidine does not contain more than about 5% of crystalline beta-L-2'-deoxythymidine.

10. The amorphous beta-L-2'-deoxythymidine of claim 2, wherein the amorphous beta-L-2'-deoxythymidine does not contain more than about 4% of crystalline beta-L-2'-deoxythymidine.

11. The amorphous beta-L-2'-deoxythymidine of claim 2, wherein the amorphous beta-L-2'-deoxythymidine does not contain more than about 3% of crystalline beta-L-2'-deoxythymidine.

12. The amorphous beta-L-2'-deoxythymidine of claim 2, wherein the amorphous beta-L-2'-deoxythymidine does not contain more than about 1% of crystalline beta-L-2'-deoxythymidine.

13. The method of claim 8, wherein the compound is administered in a pharmaceutically acceptable carrier.

14. The method of claim 13, wherein the carrier is suitable for oral delivery.

15. The method of claim 8, wherein the compound is administered in the form of a tablet, pill or capsule.

* * * * *